United States Patent [19]
Rieman et al.

[11] Patent Number: 6,061,597
[45] Date of Patent: May 9, 2000

[54] METHOD AND DEVICE FOR HEALING BONE FRACTURES

[75] Inventors: Robert D. Rieman, 225 Rockridge Cir., Durango, Colo. 81301; Roger L. Wilson, Durango, Colo.

[73] Assignee: Robert D. Rieman, Durango, Colo.

[21] Appl. No.: 09/216,060

[22] Filed: Dec. 18, 1998

Related U.S. Application Data

[60] Provisional application No. 60/068,190, Dec. 19, 1997.

[51] Int. Cl.⁷ ........................................................ A61N 1/40
[52] U.S. Cl. .............................................. 607/51; 607/52
[58] Field of Search .................................. 607/50, 51, 52

[56] References Cited

U.S. PATENT DOCUMENTS

| | | |
|---|---|---|
| 5,038,780 | 8/1991 | Boetzkes . |
| 5,273,028 | 12/1993 | McLeod et al. . |
| 5,324,314 | 6/1994 | Boetzkes . |

OTHER PUBLICATIONS

Blank, M., Biological effects of environmental electromagnetic fields: molecular mechanisms, J. Bio. and Information Processing Sciences, vol. 35, Nos. 2–3, pp. 175–178, (1995).

Al–Holou, et al., Development of a Microcomputer–based System to Monitor Healing from Injury, Biomedical Sciences Instrumentation, 35th Annual Rocky Mountain Bioengineering Symposium, Apr. 17–19, 1998, vol. 34, pp. 181–185 (1998).

Tower, et al., Resonant Frequency Analysis of the Tibia as a Measure of Fracture Healing, J. Orthop. Trauma, vol. 7., No. 6, pp. 552–557 (1993).

Halmovici, Influence of the Neoformation of Bone Tissue by Means of Low–Frequency Pulsed Magnetic Fields, Biomedical Thermology, Proceedings of an international Symposium Held in Strasbourg, France, Jun. 30–Jul. 4, 1981 (1981) Alan R. Liss, Inc., New York.

*Primary Examiner*—Scott M. Getzow
*Attorney, Agent, or Firm*—Jones & Askew, LLP

[57] ABSTRACT

Methods for healing bone fractures are provided. The methods as provided herein involve the application of resonant frequency stimulation to promote fracture healing and also to diagnose status of fracture healing. The methods of the present invention are particularly desirable because they are site-specific, non-invasive and require a minimum amount of early healing or callus formation.

14 Claims, 3 Drawing Sheets

METHOD AND DEVICE FOR HEALING BONE FRACTURES

RELATED APPLICATIONS

The present application claims priority to Provisional Application No. 60/068,190, filed Dec. 19, 1997.

FIELD OF THE INVENTION

The present invention is related to methods and devices for using resonant frequency mechanical stimulation for therapeutic purposes for healing and accelerating healing of bone fractures, and other bone-related disorders. The methods and devices of the present invention are also related to diagnostic applications of resonant frequency stimulation such as for determining the severity of fractures, and for determining degree of fracture healing. The methods and devices of the present invention are particularly desirable because they are site-specific, non-invasive and require a minimum amount of early healing or callus formation.

BACKGROUND OF THE INVENTION

It has been known for nearly 50 years that bone is piezoelectric, and that stress-strain of bone creates small voltage potentials which encourage and direct the deposition of various calcium salts. Interestingly, when bone is deformed within its elastic limits, the concave side becomes the cathode (electronegative) and all new bone deposition occurs here as opposed to the anode side. It is through this mechanism that a fractured bone heals.

Over the years investigators have claimed the value of intermittent mechanical loading in promoting and insuring fracture healing. Numerous devices have been developed to direct external voltage via implanted electrodes or by external stimulation using pulsed electromagnetic fields. Most of these applications typically employ externally applied voltage but frequently employ invasive procedures.

Systems that facilitate the healing of traumatized tissue and broken or fractured bone have been described, for example, by Boetzkes in U.S. Pat. Nos. 5,038,780 and 5,324,314. Such systems generally involve establishing an electric field between a pair of electrodes positioned on opposite sides of a patient site, resulting in the production of an alternating current having a desired frequency and amplitude characteristic in the tissue or bone. Such systems usually include a resonator formed by an inductor coupled in series with the resistor and capacitor of an equivalent circuit representing the patient site, the electrodes and any gaps therebetween. The resonator is run by an oscillator and also includes a capacitor.

Another method for promoting bone tissue growth and healing of bone tissue is described by McLeod et al. in U.S. Pat. No. 5,273,028. McLeod et al. provide an apparatus for applying a mechanical load to the bone tissue at a relatively low level on the order of between 50 and 500 microstrain peak-to-peak, and at a relatively high frequency in the range of about 15 and 55 Hz. The apparatus essentially consists of a rigid plate or area sufficient to support a patient's body when the spine is upright. The plate is supported by a stiffly compliant means and one or more transducers beneath the plate are provided to vertically drive the plate with referencing reaction to the relatively rigid support. The arrangement of a spring with the compliant means together with the plate-supported body mass is such that a naturally resonant frequency in the range of 10 Hz to 50 Hz is exhibited.

As described by M. Blank (Biosystems 35:175–178 (1995), medical studies have shown that application of low frequency electromagnetic fields accelerate the healing of bone fractures. Other studies such as one by Al-Holou (Biomedical Sciences Instrumentation 34:181–185 (1998)) confirm that induction of electric current in bone not only prevents the bone loss of functional disuse, but also induces new bone formation. As described by Al-Holou, the overall consensus in the medical community is that the skeletal response is optimal at a distinct frequency range of 10–30 Hz. It is thought that applications of very low strains may generate an effective osteogenic stimulation.

Research has demonstrated that the resonant frequency of a partially healed bone is considerably lower than that of a completely intact bone. As the healing of a fractured bone progresses, the resonant frequency rises until at full healing it matches the frequency of the opposite uninjured bone. Studies, such as those by Tower et al. (J. Orthop. Trauma 7:552–557 (1993)), demonstrated that there is a correlation between traditional parameters of tibial fracture healing and the measured resonant frequency of the healing tibia.

What is needed therefore, is a method of determining optimal frequencies of mechanical stimulation of bones, bone tissue, and bone fractures to obtain maximum healing. In addition, what is needed is a method for adjusting frequency according to the level of healing and for accommodating maximum healing through resonant frequency stimulation.

SUMMARY OF THE INVENTION

The present invention is directed to a method and device for determining optimal frequencies of electrical stimulation of bone such that a precise resonant frequency application regimen is determined and is adjusted according to the level of healing and for promoting healing. The present invention is concerned with methods of using resonant frequency mechanical stimulation of fractured bone for therapeutic purposes; to enhance and accelerate fracture healing, and for diagnostic purposes for determining the degree of fracture healing at any given time. The methods according to the present invention are site-specific, non-invasive and require a minimum amount of early healing or callus formation. The present invention is further directed to the interaction of resonance with another significant natural force, namely the piezoelectric effect in which strain and elastic deformation of certain crystalline substances (including bone) generate small voltages (1–15 millivolts, preferably 1–5 millivolts) which propagate and control the healing process.

In accordance with this invention, methods are provided for determining an optimal healing frequency regimen for mechanical stimulation of a bone, wherein the frequency is adjusted for promoting and accelerating bone healing.

Accordingly, it is an object of the present invention to provide a method of promoting and accelerating bone healing by mechanical stimulation.

It is another object of the present invention to provide a method for determining the optimal frequency of mechanical stimulation for initiating bone healing.

Yet another object of the present invention is to provide a method of bone healing such that an initial, healing frequency is determined and then adjusted according to desired resonant frequency measurements for optimizing the rate of bone healing.

Another object of the present invention is to provide a method for improving the rate of bone healing.

It is yet another object of the present invention to provide a method for monitoring bone healing.

Yet another object of the present invention is to provide a method for employing mechanical stimulation of bone tissue to prevent bone-related disorders such as osteoporosis and osteopenia.

Another object of the present invention is to provide a method for promoting bone tissue growth.

It is another object of the present invention to provide a method of mechanical stimulation of bone for maintaining bone mass and for promoting bone healing.

Yet another object of the present invention is to provide a method for the determination of the degree of long bone fracture healing through resonant frequency analysis.

Another object of the present invention is to provide a method for the acceleration of long bone fracture healing through resonant frequency stimulation.

These and other objects, features and advantages of the present invention will become apparent after a review of the following detailed description of the disclosed embodiments and the appended claims.

DETAILED DESCRIPTION

Figure 1:
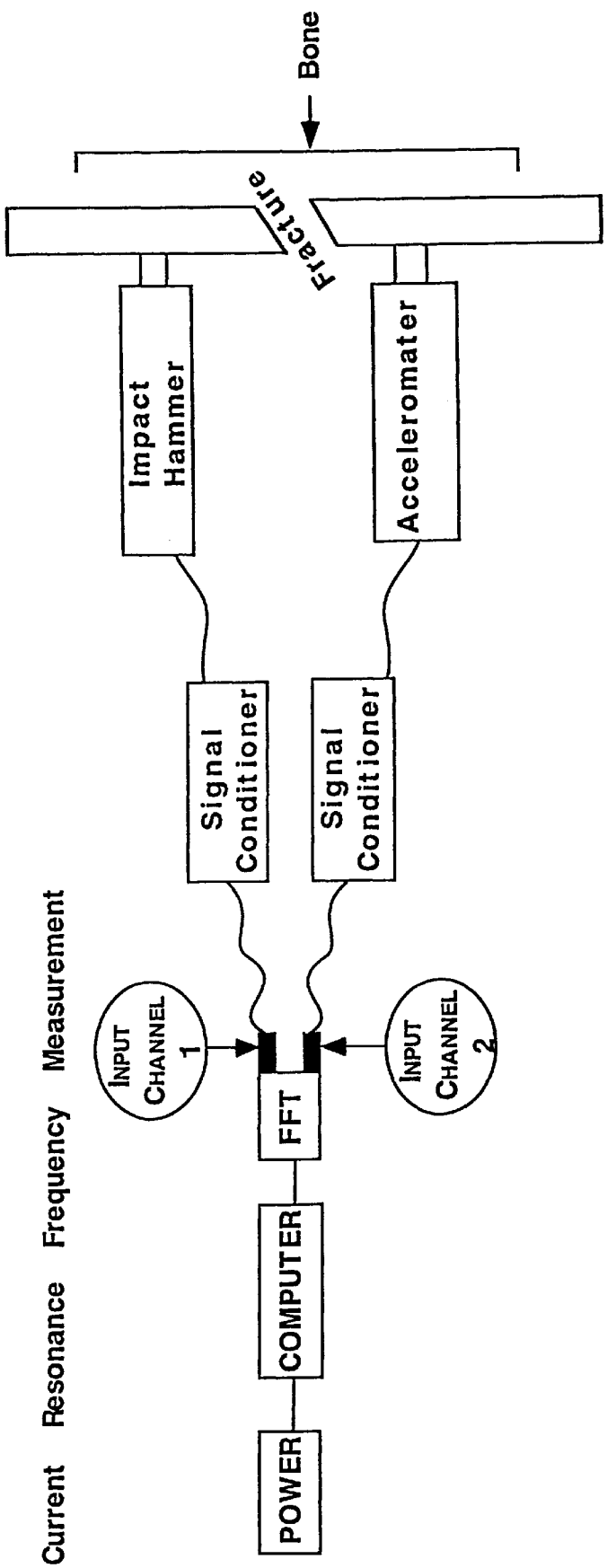
FIG. 1 is a schematic diagram showing the components required for measuring resonant frequency: impact hammer, Fast Fourier Transformer Analyzer Card (FFT), accelerometer, signal conditioners and computer.

The following description includes the best presently contemplated mode of carrying out the invention. This description is made for the purpose of illustrating the general principles of the invention and should not be taken in a limiting sense.

The novel methods of the present invention involve the generation of necessary internal voltages for bridging callus or new bone between two (or more) fragments. Unlike other methods and devices in prior art, the claimed methods are site-specific allowing new bone to be regenerated where it has the most structural significance. Importantly, this model for enhancing fracture healing more nearly imitates nature than do the prior art external voltage techniques thereby resulting in more efficient bone healing.

The method by which bone healing can be accelerated, and the degree of bone healing determined, involves resonant frequency determination for assessing degree of healing. As described in more detail below, for fracture healing acceleration, resonant frequency of the fractured bone is first determined, followed by mechanical stimulation at the resonant frequency of the fractured bone plus a small excess, for a "donkey and carrot" effect.

Resonant Frequency Determination

In one embodiment, resonant frequency determination of the present invention requires a variable frequency generator such as a standard generator or a Fast Fourier Transformer (FFT) as a part of a digital signaling process, sensor signal conditioners (preferably two), a computer, amplifiers, shaker or transducer with projecting probe, accelerometer, and an impulse force test hammer.

Resonant frequency of a bone containing a partially healed fracture is lower than that of an intact, uninjured bone. The healing process is marked by serial increases in resonant frequency. Thus, the diagnostic aspect of this device provides objective evidence of the amount and degree of bone healing as opposed to the reading of a radiograph that is an essentially subjective evaluation.

The determination of the resonant frequency of a bone may be used for assessing individual testing and for application during the course of therapy to measure changes in resonance during treatment. Individual testing requires the use of an impact hammer, and application of resonant frequency during therapy is accomplished using either an FFT or a signal generator to resonate a probe at a required frequency.

Individual testing involves the striking of a bone with an impact hammer that creates a resonance measurement from the accelerometer. The accelerometer is held non-invasively against the skin above the bone, through the FFT analyzer. A typical test result is the average of five impacts. The impact hammer and the accelerometer may be connected through individual signal conditioners to the FFT and the computer and the resonance is read on the computer screen. Resonance may be read as either force or displacement. Typical readings in the therapy model are read as force.

Use of resonant frequency determination during the course of therapy involves sending an impact signal through a transducer probe during the course of treatment. The transducer probe thus replaces the impact hammer as the source of the initial signal input. The signal may be a random burst, sine wave, or chirp and is established as periodic intervals by a computer software program especially designed to calculate the approximate signal. The impact signal is read by the accelerometer and the passes through the FFT digital signal analyzer to the computer screen. The result is the same value that would have been created by the use of the impact hammer, but there is no interruption in the therapy by virtue of using the same probe that is applying therapy.

Acceleration of Fracture Healing

According to the novel methods of the present invention, acceleration or induction of rapid healing of bone fractures involves stimulation of the partially healed bone at its current resonant frequency plus a small, (1–15 Hz) lead factor (donkey-carrot analogy). Therefore, if the resonant frequency of a fractured bone is determined to be approximately 45 Hz, then according to the present invention, bone healing therapy using mechanical stimulation comprises initial mechanical stimulation at a frequency slightly above 45 Hz, for example, 47–57 Hz. Subsequent mechanical stimulation involves a progressive and gradual increase in the frequency applied until the frequency of the bone is close to, or equivalent to, that of intact bone.

Bone as a living tissue will adapt and conform to external physical stimuli. For example, if 130 Hz represents 50% healing in a fractured tibia, then stimulation at an unvarying 130 Hz would in all likelihood preserve the 50% healing but would not promote further progression of the healing process. As was suprisingly discovered, if the stimulating frequency is slowly advanced to maintain an approximately 1–15 Hz margin above resonant frequency, then the fractured bone will continue to adapt to the new increasing frequency environment resulting in acceleration of healing.

Most importantly, the bone tissue begins to heal as it adapts to the increase in frequency. Accordingly, the novel methods of the present invention involve determination of the resonant frequency of a fractured bone and application of frequency stimulation to maintain a margin above the resonant frequency until the bone is healed.

Only at, or very close to, the resonant frequency of a partially healed fracture, is there a strong focusing of vibratory energy at the fracture site (weakest part of the bone). In a feedback mechanism it is observed that the weakest (least rigid) area is subjected to the greatest elastic deformation at its resonant frequency, leading to the greatest piezoelectric voltage generation and further leading to the greatest speed in new bone deposition at the fracture site.

The method and device of the present invention are therefore directed to promoting and accelerating bone healing by mechanical stimulation, namely resonant frequency stimulation, at a frequency range that is slightly above that of the broken bone and then subsequently modifying the frequency stimulation to accommodate and optimize bone tissue healing. The methods of the present invention may also be used to prevent bone loss and reduce bone deterioration associated with bone-related disorders such as osteoporosis and osteopenia. In addition the methods may be used for promoting bone tissue re-growth and for maintaining bone mass.

Figure 2:
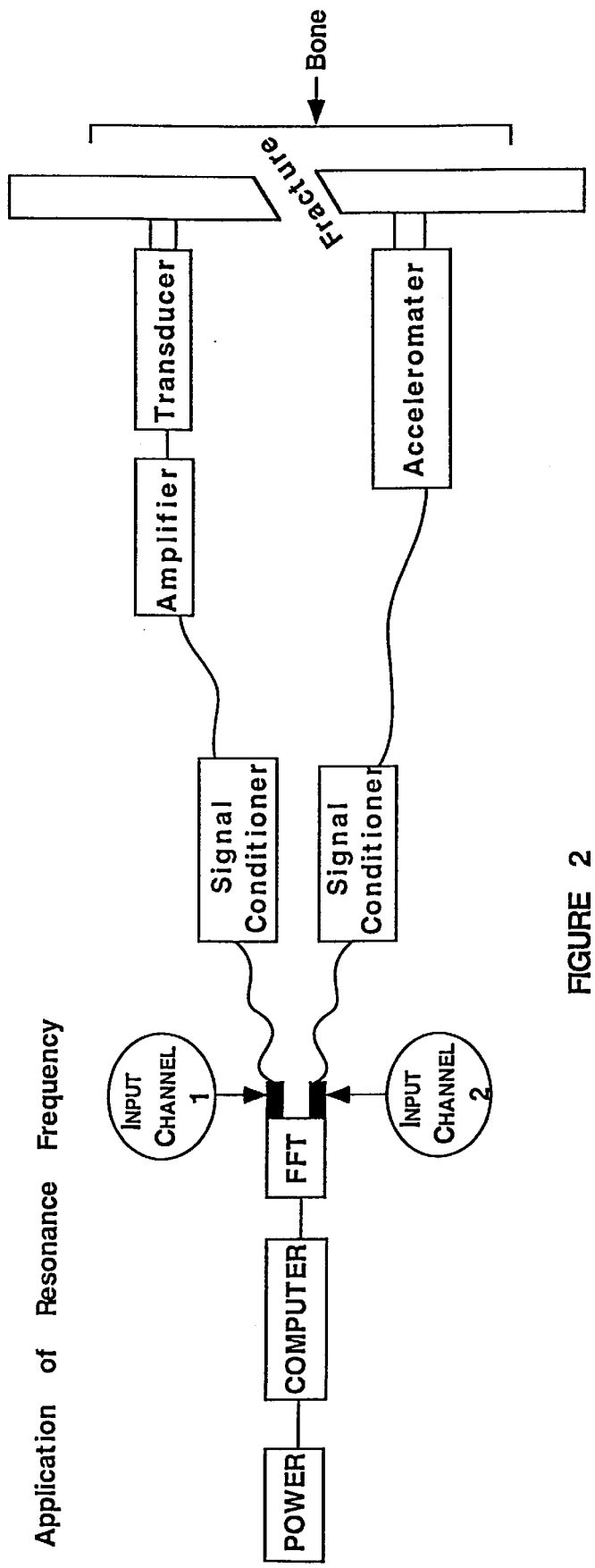
FIG. 2 is a schematic diagram showing the components required for application of resonant frequency: transducer and amplifier, Fast Fourier Transformer Analyzer Card (FFT), accelerometer, signal conditioners and computer.
Figure 3:
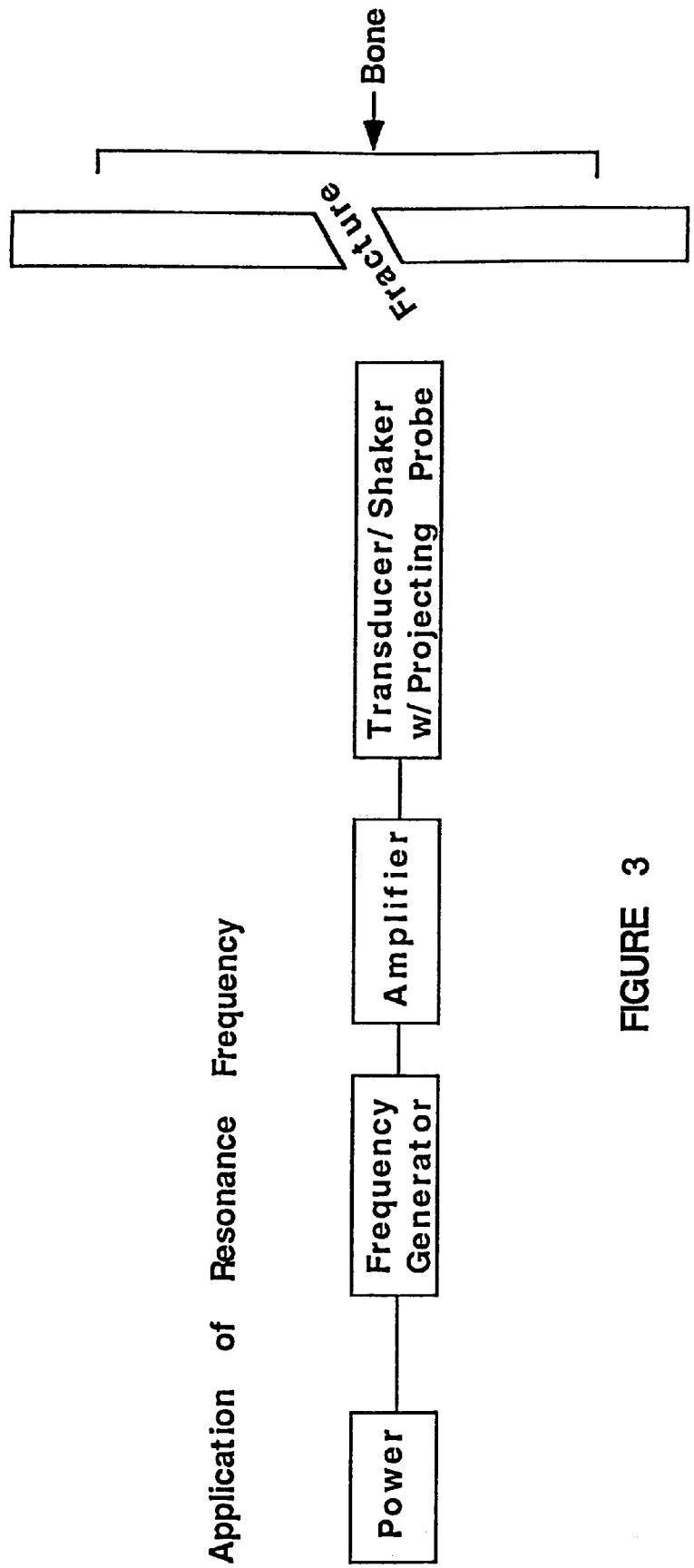
FIG. 3 is a schematic diagram showing an additional selection of components required for application of resonant frequency: frequency generator, amplifier, transducer (or shaker) with projecting probe.

Acceleration of bone healing and therapeutic intervention for bone-related disorders may be effectively accomplished non-invasively by resonant frequency application according to the methods of the present invention. In the preferred embodiment of the present invention, the principal components, required for measuring resonant frequency (as shown in greater detail in FIG. 1) include an impact hammer hooked to a Fast Fourier Transformer Analyzer Card (FFT) via an input channel, an accelerometer also hooked to the FFT via a separate input channel, signal conditioners (separately connected to the impact hammer and accelerometer and also connected to the FFT) and a computer. The FFT is configured so that it attaches to a computer port. The same components are required for application of resonance frequency, however, the impact hammer is replaced by a transducer and amplifier (as shown in FIG. 2). Alternatively, resonance frequency may be applied as shown in FIG. 3, wherein one part of a transducer (or shaker) with a projecting probe, is held against the skin near to the broken bone, and wherein another part of the transducer is connected to an amplifier which in turn is connected to a frequency generator and a power source. One preferred generator is the BK Precision, model number 3022.

The FFT is a mechanism for receiving or transmitting signals. It is capable of both measuring resonance frequency or driving a transducer at a predetermined frequency for therapy. A preferred FFT is manufactured by Data Physics and has the model number DP104.

The transducer supplies resonant frequency through the skin to the fractured bone. An important feature of the transducer is that it can be used non-invasively, i.e. it is simply held against the skin and no incision is necessary. A preferred transducer according to the present invention is custom made by modifying a speaker with a nylon probe attached to the voice coil.

Although the steps of the present invention may be conducted individually, and each of the measurements made manually, the entire procedure may be automated by use of appropriate computer software. In a preferred embodiment of the present invention, software enables the computer to receive and record input from the impact hammer via the FFT, and subsequently calculate and generate the appropriate therapeutic frequency for promoting bone repair according to the methods of the present invention through the FFT and transducer, for a predetermined period of time. At the end of resonant frequency application, the computer directs the FFT to send a burst, chirp or actual hammer signal through the probe. The accelerometer then measures the resonance frequency and, in a feedback arrangement, causes adjustment of the applied resonance accordingly.

In summary, the software optimizes resonance therapy management, recording of resonance measurements, resetting and adjustment of resonance therapy based upon correct (intact bone) measurement and may further alert a technician to any anomalies that may occur during the measurement or therapy phase. In addition, the program output can also be utilized to provide a database of information concerning the patient, fracture type, original resonance management, original resonance therapy setting, duration of therapy, subsequent resonance measurements, modifications in therapy, and physician/technician notes. The database may be centralized and made available to relevant parties by various sources such as the internet.

Theoretical calculations suggest that the four to six month time frame for fully healing a major long bone fracture might be compressed to 40–50 hours of active treatment using methods of the presently claimed invention.

Under normal fracture healing conditions a piezoelectric event might be produced by movement of a limb, muscle contraction, muscle spasm or a local systolic pulse. With resonant frequency stimulation a piezoelectric event would be a single Hertz component of that stimulating frequency. The most frequent piezoelectric event in the normal healing category is the systolic pulse 72/min. The average frequency of resonant frequency stimulation could be in the range of 100–500 Hertz.

Applied "micromotion" dynamic axial loading (dynamization), and decreasing rigidity of fixation as fractures heal (progressive destabilization) are all techniques which have been shown to enhance healing and are incorporated in various fracture treatment devices and techniques.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Effect of Resonant Frequency Stimulation on Bone Fracture

The following experiment was conducted to assess the effect of resonant frequency on bone fractures. Specifically, the effect of resonant frequency was studied with respect to healing tissue and bone composition.

Materials and Methods

The subject of this study was a one year old walker hound dog. A surgical fracture of the ulna was performed(partial fracture osteotomy) on the dog. Subsequently, twenty hours of resonant frequency stimulation was applied to the fractured ulna using a transducer modified loud speaker with a probe, an audioamplifier and a signal generator.

Histopathological studies were conducted by decalcifying samples in rapid acting decal according to methods well known in the art. Samples studied included ulna sections.

Results

The degree of healing was surprisingly high at 12 days post osteotomy. There was active remodeling in the adjacent cortex. The amount of fibrous tissue and trabecular bone formation in the osteotomy site had progressed in the correct physiological manner. There may be some increase in the amount and irregularity of spicules in the marrow cavity. There was also more tangential or parallel orientation of external callus than the radial pattern than would be expected.

Section A: Section A is a section through the cortex of the ulna that showed a gap filled with fibrous connective tissue with small islands and fine trabeculae of woven bone. There was abundant bony callus on one surface beneath an active layer of periosteal osteoblasts. The direction of the callus bone was generally perpendicular to the cortical surface. On the opposite surface (the surface with complete osteotomy) there was also abundant trabeculae of woven bone being formed. Some cartilage was present at the periphery on the one side. The orientation of this bone was generally parallel to the cortical surface rather than perpendicular.

In the deeper portion of Section A there was an increased amount of periosteal callus and islands of cartilage were found on both surfaces. Some debris was present in the defect at its base. There was active remodeling in the adjacent cortex. The area of empty osteocyte lacunae back from the osteotomy site was judged to be about normal (that is normal extent of osteocyte death). There was active osteoclastic remodeling on the osteotomy margins and active woven bone formation in the depth of the defect.

Section B is another section of cortex and contains callus adjacent to the defect site. There was an abundance of woven bone callus at the site. There was some fragmented debris in the cortical remnant. At this level there was trabeculae of woven bone occupying approximately 70% of the cortex on its inner surface. There was also increased woven bone formation throughout the marrow cavity. In the section through what is presumably the facing cortex there was a second defect seen with new bone formation on the surface (possible nutrient canal being remodeled). The defect site was filled with fibrous connective tissue and woven bone spicules. The woven bone spicules occupied approximately 50% of the defect between the ends of the cortex. Fragments of mineralized debris were encased in fibrous tissue in the marrow cavity. There was excessive formation of woven bone in the marrow cavity.

EXAMPLE 2

Effect of resonant Frequency on Healing Bone Fractures Using "Donkey-Carrot" Approach on Human Tibia This study is concerned with the use of resonant frequency mechanical stimulation of fractured bone such as human tibia for both therapeutic and diagnostic purposes. This study also explores the interaction of resonance with another significant natural force, namely the piezoelectric effect in which strain and elastic deformation of certain crystalline substances (including bone) generate small voltages (approximately 1–15 millivolts) which propagate and control the healing process.

Materials and Methods

Eight patients with simple isolated, closed fractures of their tibia or ulna (mid-diaphyseal location) that are amenable to closed treatment are eligible for the study. Criteria for entry into the study includes patients who are non-smokers with no medical conditions and/or taking medications which might alter normal fracture healing (e.g. renal osteodystrophy, cancer, epileptics taking anticonvulsants, alcoholism, nutritional deficiencies, etc.). The patients are adults (over 18 years of age) and agree to participate fully until healing of the fracture is complete or the study is discontinued at the discretion of the study investigators. Conditions for discontinuation include conditions that are harmful to the patient, or compromise study validity like delayed healing (healing time greater than two standard deviations from mean normal range), illness, equipment failure, non-compliance, adverse effects.

After initial fracture, management-closed reduction of displaced fractures and immobilization (in cast, splint or brace), the patients follow routine orthopedic procedures. At 1 to 3 weeks when initial healing callus is evident, the patients are asked to participate in the study. Four patients who are willing to participate in the treatment 'arm' of the study receive resonant frequency stimulation treatments. Healing of all patients is measured by resonant frequency analysis and radiographs as well as by clinical examination. Treatment is given five days a week, four hours per day for a total of 40 hours or less if fracture union is achieved earlier.

Resonant Procedure

In this study a variable audio frequency, or FFT generator ranging from 50 to 500 Hz, is used. The output is fed to an audio amplifier which in turn drives the transducer whose output probe is placed approximate to the bone at an accessible subcutaneous location and coupled to it through the skin for measurement purposes. The resonant vibration is detected by accelerometer created by an impact hammer or through the transducer. Analysis by microcomputer with Fast Fourier Transform (FTT) yields a spectrum of pure frequencies and their amplitudes. The highest resonance frequency in this spectrum represents the first bending mode, which is a property of bone stiffness and is used as a measure of fracture healing.

Discomforts and Risks

There should be no pain or discomfort with the use of the Resonant Frequency Stimulation (RFS) Therapy device. Should there be any discomfort, the gain (strength level) can be instantly reduced. The subject may or may not feel a mild vibration sensation. No difficulty has been encountered to date with skin irritation. Precautionary measures are routinely used, namely the use of moleskin and or tincture of benzoin or both to lower the likelihood of any skin problems.

The use of an impact hammer for measurement may produce mild soreness; however, there are few measurements in the course of treatment.

The 'control arm' of the study measures resonant frequency response in healing fractures of four patients who are not participating in resonant frequency stimulation treatment. This provides a control group of patients with fractures that heal normally (without enhancement). It also provides for comparison of resonant frequency response method of determining stage of fracture healing versus radiographs.

The initial 8 patients in this study constitute a pilot group that utilizes similar fractures treated conventionally, as described above, as the control. After the first 8 patients, a single blind placebo control is implemented if it proves feasible and compatible with the operation of the electronic equipment.

It should be understood that the foregoing relates only to preferred embodiments of the present invention, and that numerous modifications or alterations may be made therein without departing from the spirit and the scope of the invention as set forth in the appended claims. The references cited throughout are hereby incorporated by reference in their entireties.

We claim:

1. A method of promoting bone tissue regeneration comprising,
   (a) determining the frequency of damaged bone tissue;
   (b) determining the frequency of corresponding normal bone tissue;
   (c) applying resonant frequency stimulation to the damaged bone tissue wherein the resonant frequency stimulation has a frequency that is approximately 1–15 Hz above that of the frequency of the damaged bone tissue, and wherein the resonant frequency stimulation is gradually increased until it matches that of normal bone tissue.

2. The method of claim 1, wherein the damaged bone tissue comprises bone disorders selected from the group consisting of bone fractures, osteoporosis and osteopenia.

3. The method of claim 1, wherein bone tissue regeneration is related to promoting bone tissue regrowth and maintaining bone mass.

4. The method of claim 1, wherein the resonant frequency is gradually increased in increments of 2–5 Hz.

5. The method of claim 1, wherein the wherein the resonant frequency is gradually increased in increments of 4–10 Hz.

6. The method of claim 1, wherein the wherein the resonant frequency is gradually increased in increments of 8–15 Hz.

7. A method of accelerating bone tissue repair comprising,
   (a) determining the frequency of damaged bone tissue using an accelerometer;
   (b) determining the frequency of corresponding normal bone tissue using an accelerometer;
   (c) applying resonant frequency stimulation using an impact hammer to the damaged bone tissue wherein the resonant frequency stimulation has a frequency that is approximately 1–15 Hz above that of the frequency of the damaged bone tissue, and wherein the resonant frequency stimulation is gradually increased until it matches that of normal bone tissue.

8. The method of claim 7, wherein the damaged bone tissue comprises bone disorders selected from the group consisting of bone fractures, osteoporosis and osteopenia.

9. The method of claim 8, wherein the bone fracture comprises a long bone fracture.

10. The method of claim 7, wherein bone tissue regeneration is related to promoting bone tissue regrowth and maintaining bone mass.

11. The method of claim 7, wherein the resonant frequency is gradually increased in increments of 2–5 Hz.

12. The method of claim 7, wherein the wherein the resonant frequency is gradually increased in increments of 4–10 Hz.

13. The method of claim 7, wherein the wherein the resonant frequency is gradually increased in increments of 8–15 Hz.

14. A method of diagnosing degree of fracture healing comprising,
   (a) measuring the resonant frequency of a fractured bone;
   (b) measuring the resonant frequency of a normal bone corresponding to the fractured bone;
   (c) comparing the resonant frequency of the fractured bone to that of the normal bone to assess degree of healing, wherein progress in healing is indicated by resonant frequency of fractured healing corresponding approximately to resonant frequency of normal bone.

* * * * *